US012433638B1

(12) United States Patent
Wang et al.

(10) Patent No.: US 12,433,638 B1
(45) Date of Patent: Oct. 7, 2025

(54) IMPLANTATION SYSTEM AND METHOD FOR IMPLANTING FLEXIBLE NEURAL ELECTRODE

(71) Applicant: BCIFLEX MEDICAL TECHNOLOGY CO., LTD., Beijing (CN)

(72) Inventors: Jinfen Wang, Beijing (CN); Qian Li, Beijing (CN); Guiqiang Yang, Beijing (CN); Huihui Tian, Beijing (CN)

(73) Assignee: BCIFLEX MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 19/172,712

(22) Filed: Apr. 8, 2025

(51) Int. Cl.
*A61B 17/34* (2006.01)
*A61B 5/279* (2021.01)
*A61M 25/09* (2006.01)
*A61N 1/05* (2006.01)

(52) U.S. Cl.
CPC .......... *A61B 17/3468* (2013.01); *A61B 5/279* (2021.01); *A61B 17/3423* (2013.01); *A61M 25/09041* (2013.01); *A61N 1/0553* (2013.01)

(58) Field of Classification Search
CPC . A61B 17/3468; A61B 5/279; A61B 17/3423; A61M 25/09041; A61N 1/0553
See application file for complete search history.

(56) References Cited

FOREIGN PATENT DOCUMENTS

| | | |
|---|---|---|
| CN | 115054257 A | 9/2022 |
| CN | 115531719 A | 12/2022 |
| CN | 115671541 A | 2/2023 |

OTHER PUBLICATIONS

Chinese Office Action issued by the China National Intellectual Property Administration on Jul. 26, 2024 in corresponding CN Patent Application No. 202410421557.6, with English translation.

(Continued)

*Primary Examiner* — Richard G Louis
(74) *Attorney, Agent, or Firm* — Carter, DeLuca & Farrell LLP

(57) ABSTRACT

The present application provides an implantation system and method for implanting a flexible neural electrode. The implantation system comprises a flexible neural electrode and an auxiliary implantation assembly. The flexible neural electrode is provided with an auxiliary implantation part. The auxiliary implantation assembly comprises a cannula assembly and a guide wire, the cannula assembly comprises an inner cannula and an outer cannula, the guide wire has a retracted state in which it is retracted within the inner cannula and an extended state in which it penetrates out of a distal end of the inner cannula, and an extended end of the guide wire is connected to the auxiliary implantation part. Wherein, when the guide wire is in the retracted state, the flexible neural electrode is in a curled state in which it is curled between the inner cannula and the outer cannula; when the guide wire is in the extended state, the flexible neural electrode moves to an intended target area along with the guide wire and unfolds, so as to transition from the curled state to an unfolded state. The above structure can achieve the objective of implantation through a small slit on the target object, and can ensure precise implantation and flat adherence of flexible neural electrodes on the surface of the implant by strategy of the auxiliary implantation assemblies.

8 Claims, 9 Drawing Sheets

(56) References Cited

OTHER PUBLICATIONS

Chinese Office Action issued by the China National Intellectual Property Administration on Nov. 20, 2024 in corresponding CN Patent Application No. 202410421557.6, with English translation.

Notification to Grant Patent Right for Invention in corresponding Chinese Patent Application No. 202410421557.6, dated Jan. 2, 2025, with English translation.

IMPLANTATION SYSTEM AND METHOD FOR IMPLANTING FLEXIBLE NEURAL ELECTRODE

CROSS REFERENCE TO RELATED APPLICATIONS

The present application claims the benefit of and priority to Chinese Patent Application No. 202410421557.6 filed on Apr. 9, 2024, the contents of which is hereby incorporated by reference in its entirety.

TECHNICAL FIELD

The present application relates to the technical field of medical apparatus, and more specifically to an implantation system and method for implanting a flexible neural electrode.

BACKGROUND

In neuroscience research and clinical diagnosis of neurological diseases, surface array electrodes are commonly used to record or stimulate neural tissue. These electrodes can be placed on the brain, the spiral cord, or within the epidural space. Among them, the intracranial electrocorticography electrodes and spinal cord electrodes are widely used in the clinical treatment and diagnosis of neurological diseases. For example, during the diagnosis of epilepsy, intracranial neural electrodes are placed directly to the surface of the brain to perform neural monitoring and localize epileptic foci.

Currently, intracranial electrocorticography electrodes are implanted via craniotomy, while paddle-shaped spinal cord electrodes are placed in the epidural space through laminectomy. These invasive surgical approaches often result in prolonged recovery times and higher risks of postoperative complications.

SUMMARY OF THE INVENTION

In response to the above-mentioned technical problems existing in the prior art, the present application provides an implantation system and method for implanting a flexible neural electrode, which can achieve the objective of implantation through a small slit on the target object, and can ensure precise implantation and flat adherence of flexible neural electrodes on the surface of the implant by strategy of auxiliary implantation assemblies.

In a first aspect, an embodiment of the present application provides an implantation system for implanting a flexible neural electrode. The implantation system comprises:

- a flexible neural electrode on which an auxiliary implantation part is provided;
- an auxiliary implantation assembly comprising a cannula assembly and a guide wire, the cannula assembly comprises an inner cannula and an outer cannula sleeved outside the inner cannula, wherein the guide wire has a retracted state in which it is retracted within the inner cannula and an extended state in which it penetrates out of a distal end of the inner cannula, and an extended end of the guide wire is connected to the auxiliary implantation part; wherein,
- when the guide wire is in the retracted state, the flexible neural electrode is in a curled state in which it is curled between the inner cannula and the outer cannula; when the guide wire is in the extended state, the flexible neural electrode moves to an intended target area along with the guide wire and unfolds, so as to transition from the curled state to an unfolded state.

In some embodiments, the auxiliary implantation part of the flexible neural electrode is a hole or a slit.

In some embodiments, a bent part is formed at a distal end of the guide wire, and the bent part is penetrated through the auxiliary implantation part, so as to drive the flexible neural electrode to move via the guide wire.

In some embodiments, the guide wire is made of a shape memory material.

In some embodiments, when the guide wire is in the extended state, the guide wire is configured to form a target shape conforming to an outer contour of the flexible neural electrode under influence of the environment.

In some embodiments, when the length of the part of a distal end of the guide wire penetrating out of the distal end of the inner cannula is not greater than a first threshold value, the guide wire is in the retracted state; when the length of the part of the distal end of the guide wire penetrating out of the distal end of the inner cannula is greater than the first threshold value, the guide wire transitions from the retracted state to the extended state.

In some embodiments, the flexible neural electrode includes a signal transmission part and an electrode site part, and the electrode site part is electrically interconnected with a recording circuit and/or a stimulation circuit through the signal transmission part, so as to record neural signals via the recording circuit, and/or modulate neural signals via the stimulation circuit.

In some embodiments, the signal transmission part includes a plurality of flexible insulating layers and a metal signal wire layer provided between adjacent flexible insulating layers, wherein the metal signal wire layer is at least one layer, and the flexible insulating layer wraps the metal signal wire layer.

In some embodiments, the flexible insulating layer is made of a flexible polymer material, the flexible polymer material comprises at least one of polyimide materials, polymeric polymer materials, photosensitive polymers, and fluorine-containing polymers, or a combination thereof.

In some embodiments, the auxiliary implantation part is provided at a distal end of the flexible neural electrode; and/or, the auxiliary implantation part is provided at a position in the middle of or adjacent to one side of the distal end of the flexible neural electrode.

In some embodiments, a proximal end of the inner cannula is provided with a first connection structure connected to a proximal end of the guide wire, so as to define a relative position of the guide wire and the inner cannula during implantation process; and/or,

- a proximal end of the outer cannula is provided with a second connection structure connected to the proximal end of the inner cannula, so as to define a relative position of the outer cannula and the inner cannula during the implantation process.

In a second aspect, an embodiment of the present application provides an implantation method for an implantation system, it is applied to the above-mentioned implantation system for implanting the flexible neural electrode.

The implantation method comprises:

- guiding the flexible neural electrode to reach a first target area of a target implant via the auxiliary implantation assembly;

extending a distal end of the guide wire from the distal end of the inner cannula to transition the guide wire from the retracted state to the extended state;

guiding, via the guide wire, the flexible neural electrode to penetrate out from between the outer cannula and the inner cannula and reach a second target area, so as to transition the flexible neural electrode from a curled state to an unfolded state; wherein the second target area is the intended target area;

moving the inner cannula forward to the distal end of the guide wire, so that the distal end of the guide wire is detached from the auxiliary implantation part, and the flexible neural electrode is retained on a surface of the target implant;

moving the auxiliary implantation assembly away from the target implant.

In some embodiments, extending the distal end of the guide wire from the distal end of the inner cannula specifically comprises:

directly acting on the guide wire to extend the distal end of the guide wire from the distal end of the inner cannula.

In a third aspect, an embodiment of the present application provides an implantation method for an implantation system, it is applied to the above-mentioned implantation system for implanting the flexible neural electrode, and the implantation method comprises:

guiding the flexible neural electrode to reach a second target area of a target implant via the auxiliary implantation assembly; wherein the second target area is the intended target area;

acting on the outer cannula and moving the outer cannula rearward to a third target area of the target implant;

then acting on the inner cannula to move the inner cannula rearward to a fourth target area of the target implant, while the guide wire detaches from the inner cannula, enabling the guide wire to transition from the retracted state to the extended state;

guiding, via the guide wire, the flexible neural electrode to transition from a curled state to an unfolded state;

moving the inner cannula forward to a distal end of the guide wire, so that the distal end of the guide wire is detached from the auxiliary implantation part, and the flexible neural electrode is retained on a surface of the target implant;

moving the auxiliary implantation assembly away from the target implant.

In some embodiments, the fourth target area is closer to the second target area relative to the third target area.

Compared with the prior art, the beneficial effect of the embodiments of the present application is that: the present application can achieve the objective of implanting the flexible neural electrode through a relatively small slit opened on the target object by providing the cannula assembly and the guide wire. The flexible neural electrode may be precisely implanted into the intended target area after transitioning from the curled state to the unfolded state. It can be flatly adhered to the intended target area. This reduces the impact of the auxiliary implantation assembly on the surface of the target implant, and enables the low-damage and precise implantation of the flexible neural electrode, thereby addressing the existing challenges associated with the implantation of the flexible neural electrode, namely significant damage and difficulty in achieving flat adherence.

BRIEF DESCRIPTION OF THE DRAWINGS

In the drawings, which are not necessarily drawn to scale, the same reference signs may describe similar parts in different views. The drawings generally illustrate various embodiments by way of example and not limitation, and together with the description and claims, serve to explain the disclosed embodiments. Appropriately, the same reference signs are used throughout the drawings to refer to the same or similar parts. Such embodiments are illustrative and are not intended to be exhaustive or exclusive embodiments of the present device or method.

Figure 1:
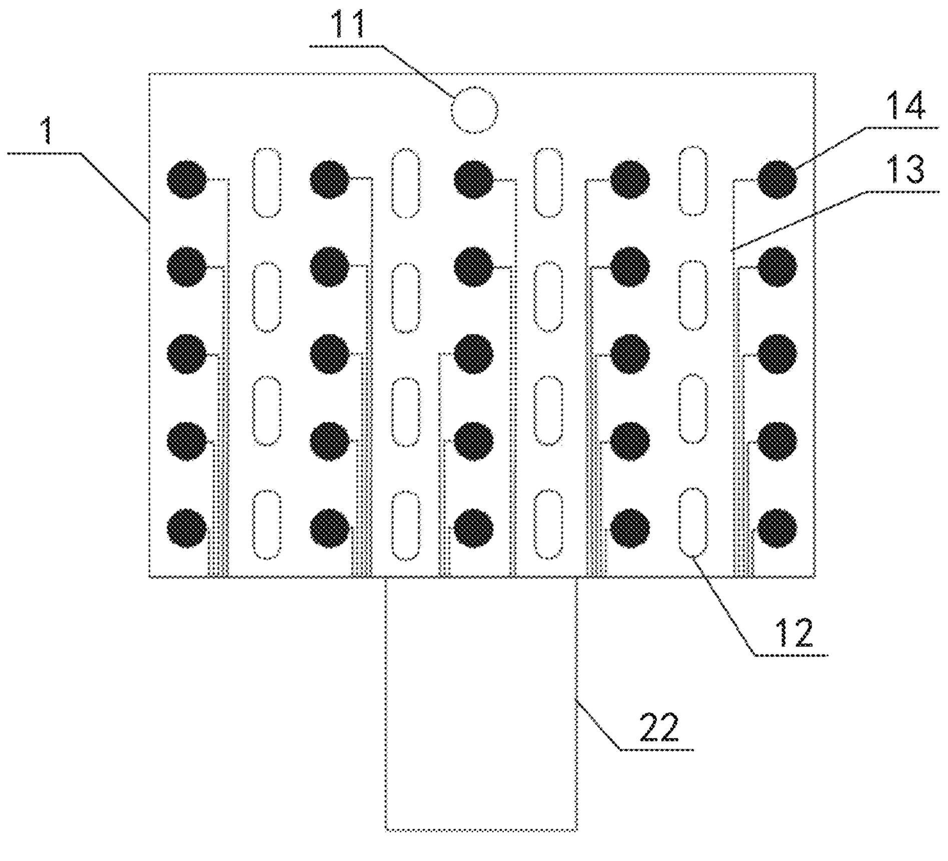
FIG. 1 is a structural schematic diagram of a flexible neural electrode for implantation system according to an embodiment of the present application, in which the flexible surface neural electrode shown is an electrocorticography electrode.

The members indicated by the reference signs in the figures:

1. flexible neural electrode; 11. auxiliary implantation part; 12. permeation hole; 13. signal transmission part; 14. electrode site part; 2. auxiliary implantation assembly; 21. cannula assembly; 211. inner cannula; 212. outer cannula; 22. guide wire; 221. bent part; 3. the first connection structure; 4. the second connection structure.

DETAILED EMBODIMENTS

In order to enable those skilled in the art to better understand the technical solution of the present application, the present application will be described in detail with reference to the drawings and specific embodiments. The embodiments of the present application will be described in further detail below with reference to the drawings and specific embodiments, but not as a limitation of the present application.

The terms "first", "second" and similar words used in the present application do not indicate any order, quantity or importance, but are only used to distinguish different parts. Similar words such as "comprising" or "containing" mean that the elements before the word cover the elements listed after the word, and the possibility of covering other elements is not excluded. "Up", "Down", "Left" and "Right" are only used to indicate the relative position relationship. When the absolute position of the described object changes, the relative position relationship may also changes accordingly.

In the present application, when it is described that a specific device is located between a first device and a second device, there may or may not be an intervening device between the specific device and the first device or the second device. When it is described that a specific device is connected to other device, the specific device may be directly connected to the other device without an intervening device, or may not be directly connected to the other device but with an intervening device.

All terms (including technical terms or scientific terms) used in the present application have the same meanings as those understood by ordinary technicians in the field to which the present application belongs, unless otherwise defined. It should also be understood that terms defined in, for example, general dictionaries should be interpreted as having meanings consistent with their meanings in the context of the related art, and should not be interpreted in an idealized or extremely formal sense unless explicitly defined here.

Techniques, methods and equipment known to those skilled in the related art may not be discussed in detail, but they should be regarded as part of the specification under appropriate circumstances.

In one embodiment of the present application, an implantation system for implanting a flexible neural electrode is provided. The implantation system for implanting the flexible neural electrode may be used in the medical field. Currently, when surface array electrodes are implanted on the brain, it is necessary to perform a craniotomy at the target position of the patient's brain, and then place the surface array electrodes to meet the requirement of flat adherence of the surface array electrodes on the cerebral plane. When implanting surface array electrodes epidurally on the spinal cord, surgical procedures such as laminectomy or laminotomy are required to place the surface array electrodes. However, these traditional surgical methods cause significant trauma and are not benefit to the patient's subsequent recovery. In order to meet the development needs of minimally invasive surgery, the present application provides an implantation system for implanting a flexible neural electrode. A detailed introduction of an implantation system for implanting a flexible neural electrode according to an embodiment of the present application will be provided below with reference to the accompanying drawings.

As shown in FIGS. 1 to 5, the implantation system for implanting the flexible neural electrode includes a flexible neural electrode 1 and an auxiliary implantation assembly 2. The flexible neural electrode 1 is provided with an auxiliary implantation part 11. The auxiliary implantation assembly 2 includes a cannula assembly 21 and a guide wire 22. The cannula assembly 21 includes an inner cannula 211 and an outer cannula 212 that is sleeved outside the inner cannula 211. The guide wire 22 has a retracted state retracted within the inner cannula 211 and an extended state that penetrates out of a distal end of the inner cannula 211. An extended end of the guide wire 22 is connected to the auxiliary implantation part 11. Wherein, when the guide wire 22 is in the retracted state, the flexible neural electrode 1 is in a curled state curled between the inner cannula 211 and the outer cannula 212; when the guide wire 22 is in the extended state, the flexible neural electrode 1 moves with the guide wire 22 to the intended target area and unfolds, so as to transition from the curled state to an unfolded state.

Figure 2:
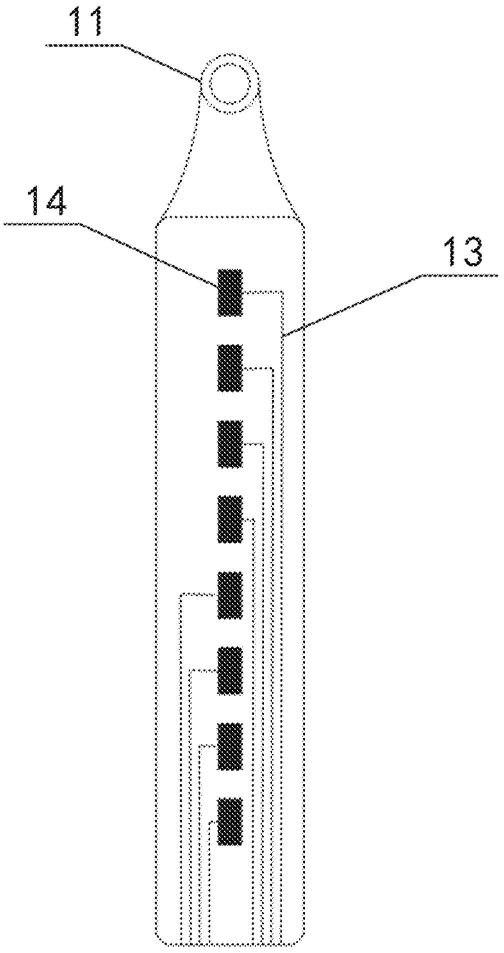
FIG. 2 is a structural schematic diagram of a flexible neural electrode for implantation system according to an embodiment of the present application, in which the flexible surface neural electrode shown is an epidural spinal cord electrode.

Optionally, the flexible surface neural electrode may be a thin-film electrode, which may be an intracranial neural electrode and spinal cord electrode processed by micro-nano fabrication technology, as well as an intracranial neural electrode and spinal cord electrode used clinically. For example, the flexible surface neural electrode may be an electrocorticography electrode, an epidural spinal cord electrode, or an electrode applied to other parts, and the present application does not make specific limitations on this. Exemplarily, as shown in FIGS. 1 and 2, the flexible surface neural electrode shown in FIG. 1 is an electrocorticography electrode, and the flexible surface neural electrode shown in FIG. 2 is an epidural spinal cord electrode.

Figure 3:
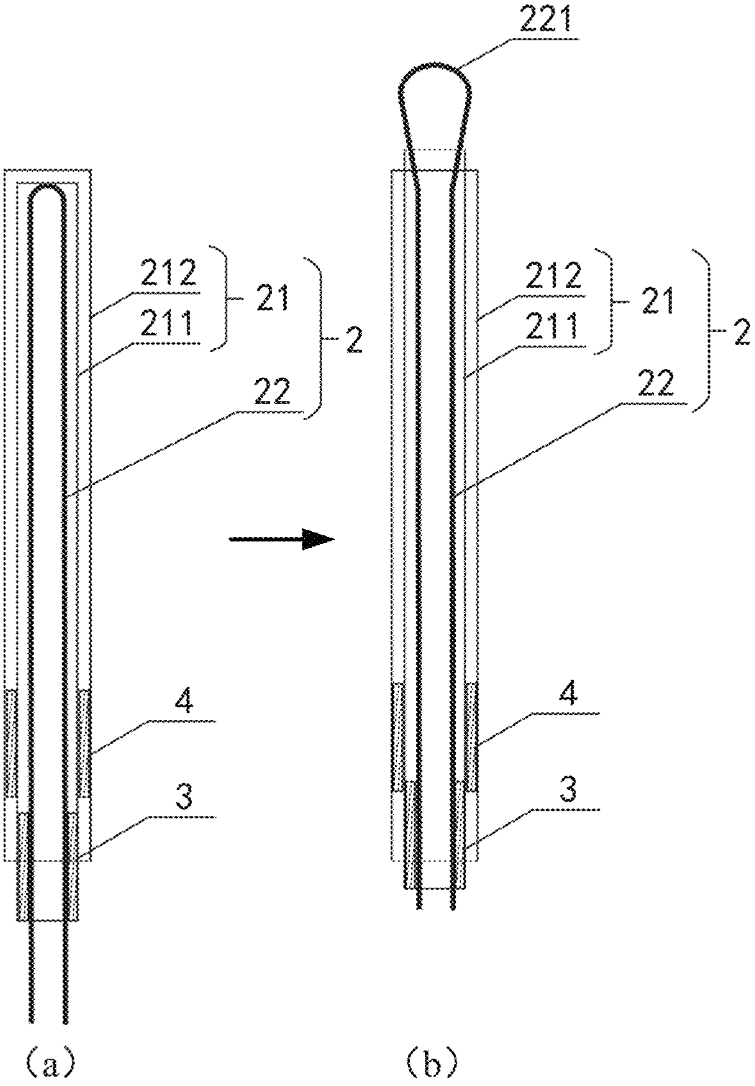
FIG. 3 is a partial structural schematic diagram of an auxiliary implantation assembly according to an embodiment of the present application, in which a guide wire shown in part (a) is in a retracted state, and a guide wire shown in part (b) partially extends out of a cannula assembly.
Figure 4:
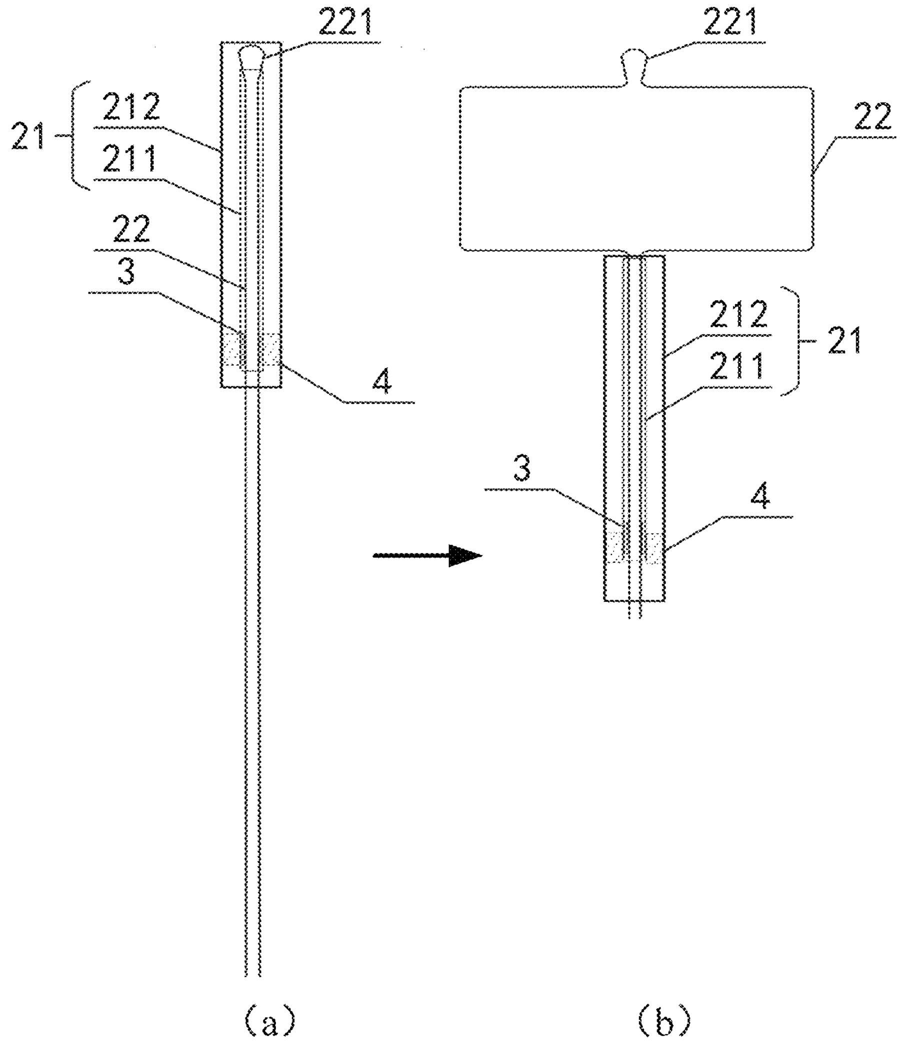
FIG. 4 is a partial structural schematic diagram of an auxiliary implantation assembly according to an embodiment of the present application, in which a guide wire shown in part (a) is in a retracted state, and a guide wire shown in part (b) is in an extended state.

As shown in FIGS. 3 and 4, the guide wire 22 shown in part (a) of FIG. 3 is in a retracted state, the guide wire 22 shown in part (b) of FIG. 3 partially extends out of the cannula assembly 21, the guide wire 22 shown in part (a) of FIG. 4 is in a retracted state, and the guide wire 22 shown in part (b) of FIG. 4 is in an extended state.

Optionally, the auxiliary implantation part 11 may be a through hole, and the number of the through holes is not less than 1. The shape of the through hole may be elliptical, circular, polygonal, or a combination of two thereof. The dimension of the through hole ranges from 0.05 mm to 10 mm, for example, 0.05 mm, 0.1 mm, 0.2 mm, 0.5 mm, 1 mm, 10 mm, etc., preferably 0.1 mm.

Optionally, the inner cannula 211 and the outer cannula 212 are pipes with hollow structures. The inner cannula 211 and the outer cannula 212 have a distal end away from the operator and a proximal end close to the operator, respectively. The distal ends of the inner cannula 211 and the outer cannula 212 are open structures, and the design of the distal opening structure of the inner cannula 211 can switch the guide wire 22 between the retracted state and the extended state without affecting the movement of the guide wire 22. The design of the distal opening structure of the outer cannula 212 can make the inner cannula 211, the guide wire 22, and the flexible neural electrode 1 retract or penetrate out of the outer cannula 212.

Optionally, the cross-sections of the inner cannula 211 and the outer cannula 212 may be elliptical, circular, polygonal, or a combination of two thereof. The diameter of the outer cannula 212 is larger than that of the inner cannula 211, and there is a gap formed between the inner wall of the outer cannula 212 and the inner wall of the inner cannula 211 for accommodating the flexible neural electrode 1.

Optionally, the diameters of the inner cannula 211 and the outer cannula 212 respectively range from 0.05 to 20 millimeters (mm), for example, 0.05 mm, 0.5 mm, 1 mm, 5 mm, 10 mm, 20 mm, etc. The diameter of the inner cannula 211 is preferably 1 mm, and the diameter of the outer cannula 212 is preferably 5 mm.

Optionally, the materials of the inner cannula 211 and the outer cannula 212 may be one or a combination of several polymer materials. Exemplarily, polymer materials may be polyimide, polyurethane, or polyvinyl chloride. The cannula assembly 21 made of polymer material can effectively reduce the damage to brain tissue in the implantation process and improve the safety of use of the implantation system.

Optionally, the diameter of guide wire 22 is 0.01 to 1 millimeter (mm), for example, 0.01 mm, 0.05 mm, 0.1 mm, 0.5 mm, 1 mm, etc., preferably 0.2 mm.

Optionally, when the above flexible neural electrode 1 is in the curled state, it may be curled between the inner cannula 211 and the outer cannula 212 in a scroll-like configuration, or may be stored between the inner cannula 211 and the outer cannula 212 in a folded arrangement. The present application does not make specific limitations on this, provided that the flexible neural electrode 1 can be stably accommodated without damage to the flexible neural electrode 1.

It is to be understood that the intended target area may be the target position where the flexible neural electrode 1 is intended to act on, and the objective of the implantation system is to implant the flexible neural electrode 1 onto the intended target area, so that it is adhered to the surface of the corresponding tissue there.

The present application can achieve the objective of implanting the flexible neural electrode through a relatively small slit opened on the target object by providing the cannula assembly 21 and the guide wire 22. The flexible neural electrode 1 may be precisely implanted into the intended target area after transitioning from the curled state to the unfolded state. It can be flatly adhered to the intended target area. This reduces the impact of the auxiliary implantation assembly 2 on the surface of the target implant, and enables the low-damage and precise implantation of the flexible neural electrode 1, thereby addressing the existing challenges associated with the implantation of the flexible neural electrode 1, namely significant damage and difficulty in achieving flat adherence.

In some embodiments, the auxiliary implantation part 11 of the flexible neural electrode 1 is a hole or a slit.

In some embodiments, as shown in FIG. 3, a bent part 221 is formed at a distal end of the guide wire 22, and the bent part 221 is penetrated through the auxiliary implantation part 11 to drive the flexible neural electrode 1 to move via the guide wire 22.

Optionally, the bent part 221 of the guide wire 22 may be anchored with the auxiliary implantation part 11, and the flexible neural electrode 1 may be driven to reciprocate by pushing and pulling the guide wire 22.

Optionally, the bent part 221 formed at the distal end of the guide wire 22 may be specifically configured in a teardrop shape, it passes through the auxiliary implantation part 11, with the dimension of the distal end of the bent part 221 being larger than that of the auxiliary implantation part 11, thereby enabling the bent part 221 to drive the flexible neural electrode 1 through the auxiliary implantation part 11.

Optionally, the guide wire 22 may be made of a flexible deformable material, and the above bent part 221 can flexibly drive the flexible neural electrode 1 to move when subjected to a relatively small applied force. The bent part 221 can also deform after being subjected to force to detach from the auxiliary implantation part 11, thereby releasing the effect on the flexible neural electrode 1.

In the above embodiment, the bent part 221 of the guide wire 22 may be used to conveniently and precisely control the movement of the flexible neural electrode 1, thereby effectively improving the accuracy and convenience of the implantation system for implanting the flexible neural electrode.

In some embodiments, the guide wire 22 is made of a shape memory material. The guide wire 22 made of the above shape memory material may undergo deformation after the surrounding environment meets the preset conditions, such as the temperature condition can meet the preset temperature, and the shape of the guide wire 22 can assume the preset shape without arbitrary shape variations. It can be understood that the guide wire 22 made of the shape memory material can recover its original shape after experiencing deformation, thereby ensuring that the flexible neural electrode 1 can be flatly unfolded under the guidance of the deformed shape of the guide wire 22.

Optionally, the shape memory material may be a shape memory polymer, a shape memory alloy, etc. Exemplarily, the shape memory alloy may be a nickel-cobalt alloy shape memory alloy or a nickel-titanium shape memory alloy, etc.

Optionally, the surface of the guide wire 22 may be wrapped with an outer insulating layer to keep the surface of the guide wire 22 flat and avoid destructive damage to the flexible neural electrode 1 caused by the guide wire 22.

In the above embodiment, the flexible neural electrode 1 may be conveniently and precisely controlled to adhere to the intended target area through the guide wire 22 made of shape memory material, thereby effectively ensuring the accuracy and convenience of the implantation system for implanting the flexible neural electrode.

In some embodiments, as shown in FIG. 4, when the guide wire 22 is in the extended state, the guide wire 22 is configured to form a target shape conforming to an outer contour of the flexible neural electrode 1 under the influence of the environment.

When the guide wire 22 extends from the distal end of the inner cannula 211, the shape of the guide wire 22 may be changed to a target shape conforming to the outer contour of the flexible neural electrode 1, thereby improving the stability between the guide wire 22 and the flexible neural electrode 1, reducing the possibility of displacement or detachment between the two, and ensuring that the flexible neural electrode 1 can be flatly unfolded when the operator uses the implantation system.

Exemplarily, as shown in FIG. 4, the target shape of the extended guide wire 22 shown in FIG. 4 conforms to the outer contour of the electrocorticography electrode.

In the above embodiment, the guide wire 22 has a target shape conforming to the outer contour of the flexible neural electrode 1 when it is in the extended state, enabling the flexible neural electrode 1 to be flatly and smoothly unfolded under the guidance of the guide wire 22 with the target shape after extending out of the outer cannula 212, which can effectively ensure the reliability of the implantation system for implanting the flexible neural electrode and improve the accuracy and experience of the operator's operation. In addition, the guide wire 22 conforming to the outer contour of the flexible neural electrode 1 can make the implantation surgery simpler and more precise, effectively reducing the operational risk and time, and increasing the success rate of the surgery.

In some embodiments, as shown in FIG. 4, when a length of the part of the distal end of the guide wire 22 penetrating out of the distal end of the inner cannula 211 is not greater than a first threshold value, the guide wire 22 is in the retracted state; when the length of the part of the distal end of the guide wire 22 penetrating out of the distal end of the inner cannula 211 is greater than the first threshold value, the guide wire 22 transitions from the retracted state to the extended state.

In this way, the guide wire 22 can transition from the retracted state to the extended state only after extending a certain length, and it does not change state immediately upon extension, ensuring the stability of the state change of the guide wire 22.

In the above embodiment, by controlling the length of the part of the distal end of the guide wire 22 penetrating out of the distal end of the inner cannula 211, the switching of the guide wire 22 between the retracted state and the extended state can be flexibly and precisely controlled, effectively improving the accuracy and controllability of the operation in the implantation process.

In some embodiments, as shown in FIGS. 1 and 2, the flexible neural electrode 1 includes a signal transmission part 13 and an electrode site part 14. The electrode site part 14 is electrically interconnected with a recording circuit and/or a stimulation circuit through the signal transmission part 13, so as to record neural signals via the recording circuit, and/or modulate neural signals via the stimulation circuit.

Optionally, the electrode site part 14 may be one or more, and the electrode site part 14 can transmit electrical signals with external equipment through the signal transmission part 13 connected thereto.

Optionally, the constituent material of the electrode site part 14 is conductive metal or conductive polymer. Exemplarily, it may be gold, platinum, iridium, platinum-iridium alloy, carbon composite material, or PEDOT: PSS (poly (3,4-ethylenedioxythiophene) and poly (styrene sulfonic acid)) conductive polymer, etc. For the convenience of expression and understanding, the poly (3,4-ethylenedioxythiophene) and poly (styrene sulfonic acid) conductive polymer is directly referred to as PEDOT: PSS conductive polymer hereinafter.

Optionally, the shape of the electrode site part 14 may be circular, square, rectangular, hexagonal, or rhombic, etc., preferably circular. The circular structure has the most stable diffusion pattern when measuring neural signals.

Optionally, the diameter of the electrode site part 14 may range from 0.01 to 5 millimeters (mm), and may be 0.01 mm, 0.1 mm, 0.5 mm, 1 mm, 2 mm or 5 mm, etc.

Optionally, the electrode site part 14 may be arranged in an array or randomly arranged according to experimental requirements. The spacing between a plurality of electrode site parts 14 may range from 0.01 to 5 millimeters (mm), which may be 0.01 mm, 0.1 mm, 0.5 mm, 1 mm, 2 mm, or 5 mm, etc.

Optionally, the plurality of electrode site parts 14 may have the same dimensions, or have different dimensions respectively.

Optionally, permeation holes 12 may be provided around the electrode site part 14, which can facilitate the penetration and permeation of the auxiliary adherence liquid, ensuring good adherence between the flexible neural electrode 1 and the target implant.

Optionally, the shape of the permeation holes 12 may be circular, elliptical, rectangular, square, etc. The dimension of the permeation hole 12 may range from 0.1 to 10 millimeters (mm), which may be 0.1 mm, 0.5 mm, 1 mm, 5 mm, or 10 mm, etc.

The dimension of electrode site part 14, the site shape of the electrode site part 14, the spacing between the plurality of electrode site parts 14, and the arrangement of the permeation holes 12 may be determined and arranged according to actual needs. The embodiments disclosed in the present application do not make any limitations on this.

In the above embodiment, the electrode site part 14 is connected to the recording circuit and the stimulation circuit through the signal transmission part 13, and the signal output of the electrode site part 14 can be monitored and recorded in real time, and more precise control can be achieved by adjusting the parameters of the stimulation signal, thereby effectively ensuring the use effect of the implantation system for implanting the flexible neural electrode.

In some embodiments, the signal transmission part 13 includes a plurality of flexible insulating layers and a metal signal wire layer provided between adjacent flexible insulating layers. The metal signal wire layer is at least one layer, and the flexible insulating layer wraps the metal signal wire layer.

Optionally, there may be a plurality of metal signal wire layers, which are arranged in a stacked manner. Moreover, a flexible insulating layer is provided between adjacent metal signal wire layers, which can integrate more electrode site parts 14 while reducing the dimension of the flexible neural electrode 1, and can effectively reduce interference between neural signals.

Optionally, the number of the metal signal wire layers is set corresponding to the number of the electrode site parts 14, and the plurality of electrode site parts 14 are respectively connected to its corresponding metal signal wire layers. The plurality of metal signal wire layers are insulated from each other by flexible insulating layers.

Optionally, the metal signal wire layer may be composed of one or more conductive materials selected from precious metals, conductive metals, or conductive polymers. Exemplarily, conductive materials may be gold, platinum, iridium, platinum-iridium alloy, carbon composite material or PEDOT: PSS conductive polymer, etc.

In the above embodiment, by providing the flexible insulating layers between the metal signal wire layers and wrapping the metal signal wire layers with flexible insulating layers, mutual interference between neural signals can be effectively prevented, and the anti-interference capability and accuracy of neural signal transmission can be improved.

Taking the intracranial neural electrode and spinal cord electrode processed by micro-nano fabrication technology, in where the insulating part is polyimide, the electrode site part 14 and the metal signal wire layer are made of gold, as an example, the manufacturing process of the thin-film electrode is described. The thin-film electrode adopts a hard substrate, such as glass, quartz, silicon wafer, etc., as a supporting material of the thin-film electrode to meet the flatness requirements of the thin-film electrode. A sacrificial layer of the thin-film electrode is processed on the substrate, for instance, a layer of removable material, such as an aluminum layer or a nickel layer, is added, which can separate the thin-film electrode from the substrate. The flexible insulating layer polyimide is processed on the substrate by a film forming technology. The polyimide may be photosensitive or non-photosensitive polyimide, and the photosensitive polyimide requires spin-coating, baking, and subsequent photolithography patterning to form a film, while the non-photosensitive polyimide requires spin-coating, baking, and imidization under high-temperature vacuum environment to form a film. The metal signal wire layer is patterned using photoresist, followed by deposition of a gold layer via magnetron sputtering or evaporation to obtain patterned electrode site parts 14 and metal signal wire layers. Then, the same method is used to process the second layer of flexible insulating layer. If a plurality of metal signal wire layers and flexible insulating layers are required, the above process may be repeated. The plurality of flexible insulating layers and metal signal wire layers can integrate more electrode site parts 14 while reducing the dimension of the electrode, and can achieve high-density integration of the flexible neural electrodes 1. The exposure and the overall patterning of the electrode site parts 14 of the flexible neural electrode 1 are achieved by the patterning of polyimide. Photosensitive polyimide requires patterning by photolithography, and non-photosensitive polyimide requires to be patterned by dry or wet etching.

In some embodiments, the flexible insulating layer is made of a flexible polymer material, which at least includes one or a combination of more of polyimide materials, polymeric polymer materials, photosensitive polymers, and fluorine-containing polymers. Wherein, the above-mentioned fluorine-containing polymers may specifically be fluororesin.

Exemplarily, the flexible polymer material may be polyimide, SU-8 (epoxy-based negative photoresist), parylene, or silicone rubber, etc.

Flexible polymer materials have good insulating properties and can effectively prevent signal interference between metal signal wires. Flexible polymer materials have good flexibility and bendability, and can adapt to different shapes and curved surfaces, allowing the flexible insulating layer to flexibly cover the metal signal wire layer to provide effective insulation protection.

In the above embodiment, the flexible insulating layer made of flexible polymer materials can effectively improve the stability and anti-interference capability of neural signal transmission, thereby enhancing the reliability of the implantation system for implanting the flexible neural electrode.

In some embodiments, as shown in FIGS. 1 and 2, the auxiliary implantation part 11 is provided at a distal end of the flexible neural electrode 1; and/or, the auxiliary implantation part 11 is provided at a position in the middle of or adjacent to one side of the distal end of the flexible neural electrode 1.

The structure of the intended target area may vary among different patients, and individual adaptation may be performed according to the patient's different conditions, which helps to improve the adherence between the flexible neural electrode 1 and the intended target area, thereby reducing the damage and risk during implantation process.

In the above embodiment, the auxiliary implantation part 11 may be flexibly arranged on the flexible neural electrode 1 according to different usage scenarios and requirements, effectively improving the universality of the implantation system for implanting the flexible neural electrode.

In some embodiments, a proximal end of the inner cannula 211 is provided with a first connection structure 3 connected to a proximal end of the guide wire 22, so as to define the relative position of the guide wire 22 and the inner cannula 211 during the implantation process; and/or, a proximal end of the outer cannula 212 is provided with a second connection structure 4 connected to a proximal end of the inner cannula 211, so as to define the relative position of the outer cannula 212 and the inner cannula 211 during the implantation process.

It can be understood that the guide wire 22 and the inner cannula 211 are fixed through the first connection structure 3 during the implantation process. The guide wire 22 can move axially along the inner cannula 211 and can penetrate out and retract at the distal end of the inner cannula 211. Penetrating out is indicated by the bent part 221 of the guide wire 22 penetrating out from the distal end of the cannula. The guide wire 22 that penetrates out can be mutually anchored with the flexible neural electrode 1 through the auxiliary implantation part 11, thereby achieving the fixation of the flexible neural electrode and the auxiliary implantation assembly 2. Retraction is indicated by the bent part 221 of the guide wire 22 retracting into the interior of the inner cannula 211 through the distal end, and the guide wire 22 and the auxiliary implantation part 11 of the flexible neural electrode 1 are detached from each other.

A second connection structure 4 is provided between the proximal end of the outer cannula 212 and the proximal end of the inner cannula 211, and the moving position of the inner cannula 211 is precisely fixed by means of the second connection structure 4 during the implantation process.

In the above embodiment, through the first connection structure 3 and the second connection structure 4, the displacement of the guide wire 22 and the inner cannula 211 during implantation process can be restricted, which effectively improves the safety of the cannula assembly 21, and further improves the reliability and safety of the implantation system for implanting the flexible neural electrode.

The embodiment of the present application also provides an implantation method for an implantation system, which is applied to the above-mentioned implantation system for implanting the flexible neural electrode.

Figure 8:
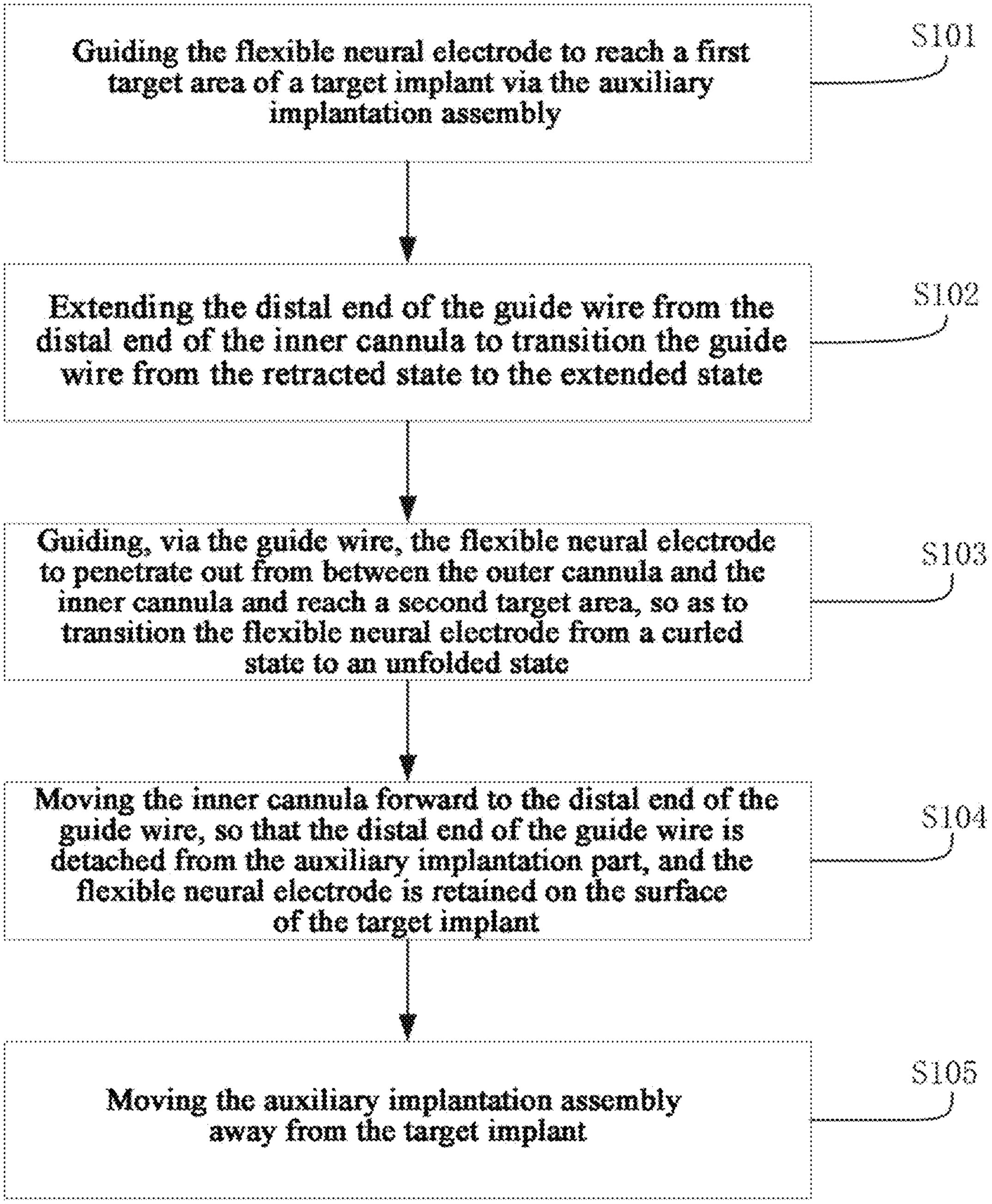
FIG. 8 is a first flowchart of an implantation method for an implantation system according to an embodiment of the present application.

As shown in FIG. 8, the implantation method includes steps S101 to S105.

Step S101: guiding the flexible neural electrode 1 to reach a first target area of the target implant via the auxiliary implantation assembly 2.

Step S102: extending the distal end of the guide wire 22 from the distal end of the inner cannula 211 to transition the guide wire 22 from the retracted state to the extended state.

Step S103: guiding, via the guide wire 22, the flexible neural electrode 1 to penetrate out from between the outer cannula 212 and the inner cannula 211 and reach a second target area, so as to transition the flexible neural electrode 1 from a curled state to an unfolded state; wherein, the second target area is the intended target area.

Step S104: moving the inner cannula 211 forward to the distal end of the guide wire 22, so that the distal end of the guide wire 22 is detached from the auxiliary implantation part 11, and the flexible neural electrode 1 is retained on the surface of the target implant.

Step S105: moving the auxiliary implantation assembly 2 away from the target implant.

Figure 5:
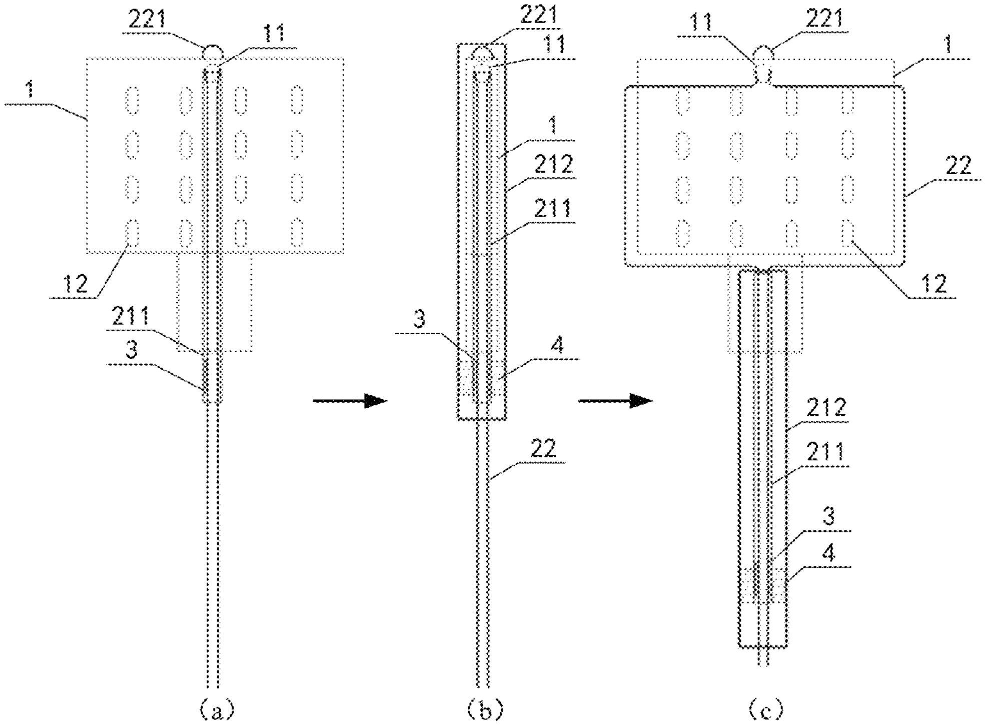
FIG. 5 is a schematic diagram of part of operations of an implantation method for an implantation system according to a first embodiment of the present application.
Figure 6:
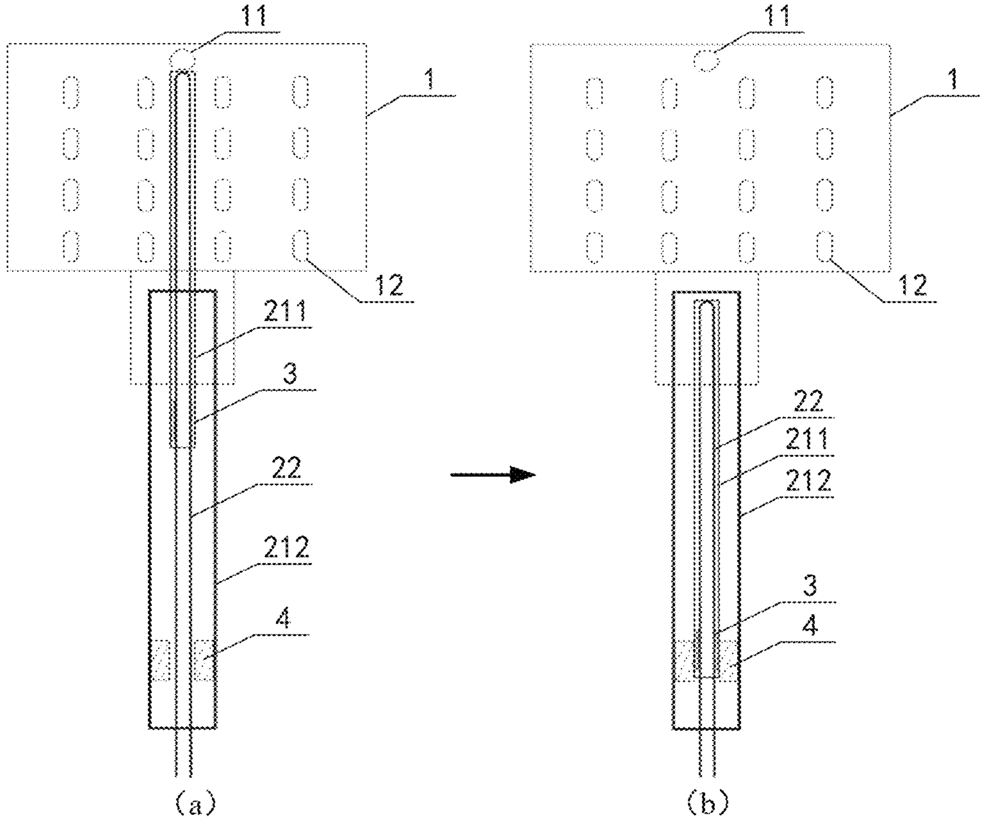
FIG. 6 is a schematic diagram of the other part of operations of the implantation method for the implantation system according to the first embodiment of the present application.
Figure 7:
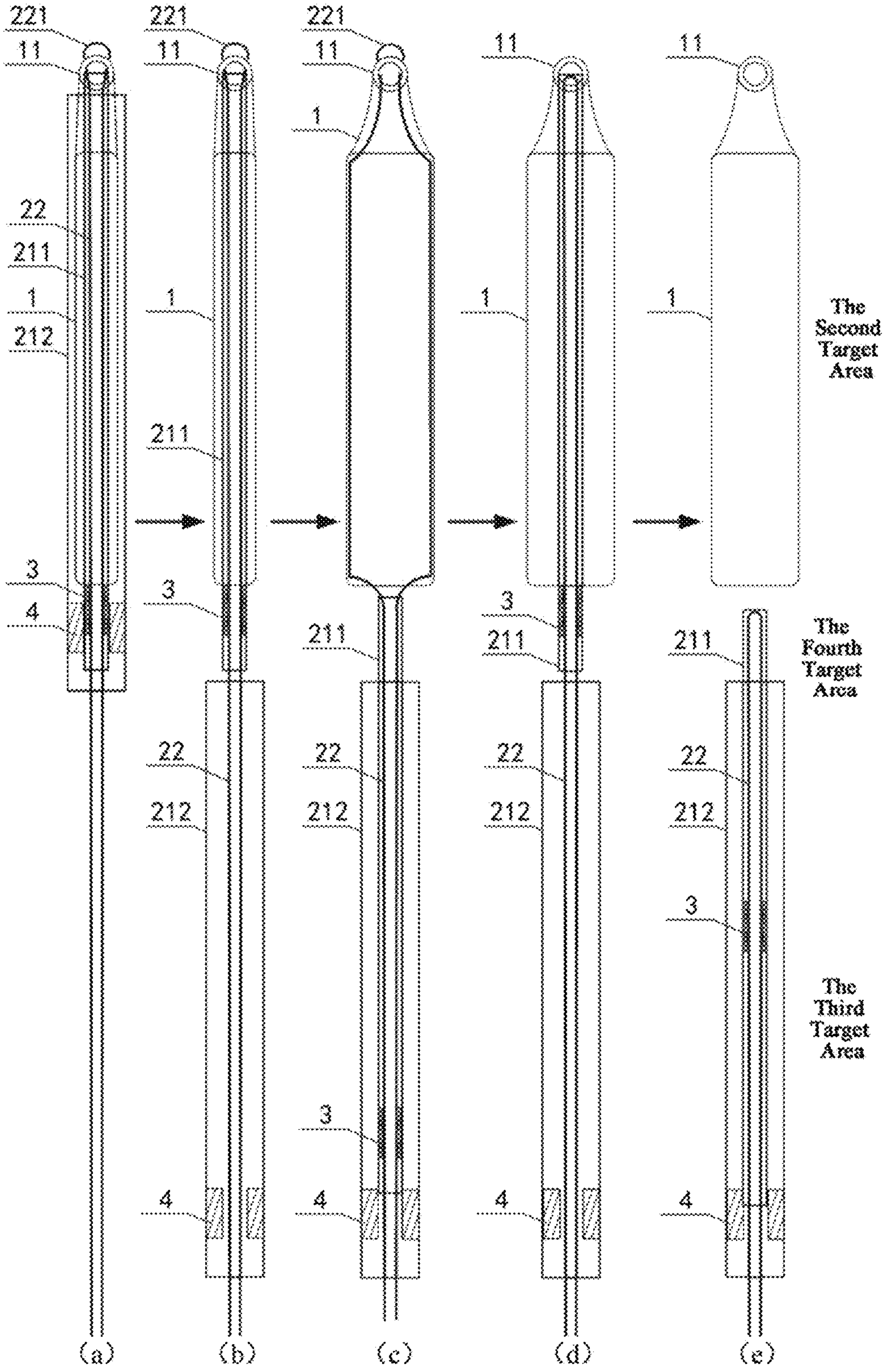
FIG. 7 is a schematic diagram of operations of an implantation method for an implantation system according to a second embodiment of the present application.

As shown in FIGS. 5 to 7, the implantation system for implanting the flexible neural electrode is exemplified as flexible electrocorticography electrodes implanted on the surface of the brain. As shown in part (a) of FIG. 5, the inner cannula 211 and the guide wire 22 retracted into the inner cannula 211 are placed on the front or back of the electrode site part 14 of the flexible neural electrode 1, and aligned with the auxiliary implantation part 11 of the flexible neural electrode 1. After alignment, the guide wire 22 is moved axially from the proximal end of the inner cannula 211 to the distal end of the inner cannula 211 until the guide wire 22 penetrating out of the distal end of the inner cannula 211 is anchored to the auxiliary implantation part 11 of the flexible neural electrode 1, and the proximal guide wire 22 and the proximal end of the inner cannula 211 are fixed by means of the first connection structure 3. As shown in part (b) of FIG. 5, the flexible neural electrode 1 is curled around the inner cannula 211, and the outer cannula 212 provides spatial structural constraint to the curled flexible neural electrode 1. The proximal end of the outer cannula 212 and the proximal end of the inner cannula 211 are fixed by means of the second connection structure 4, forming a composite structure of the flexible neural electrode 1 and the auxiliary implantation assembly 2.

As shown in part (c) of FIG. 5, the above composite structure of the flexible neural electrode 1 and the auxiliary implantation assembly 2 is implanted into the first target area of the target implant through a skull slit or puncture needle. The first connection structure 3 between the proximal end of the inner cannula 211 and the proximal end of the guide wire 22 is unlocked. The proximal end of the guide wire 22 is moved axially toward the distal end, and the distal end of the guide wire 22 is extended from the distal end of the inner cannula 211, guiding the flexible neural electrode 1 to penetrate out of the outer cannula 212. After the extended part of the guide wire 22 exceeds the first threshold, the guide wire 22 is transitioned from the retracted state to the extended state, thereby driving the curled flexible neural electrode 1 to reach the second target area and unfold flatly.

As shown in part (a) of FIG. 6, after the flexible neural electrode 1 is fully unfolded as shown in part (c) of FIG. 5, the second connection structure 4 between the proximal end of the outer cannula 212 and the proximal end of the inner cannula 211 is unlocked, and the inner cannula 211 is moved forward until it reaches the distal end of the guide wire 22; the distal end of the guide wire 22 is retracted into the inner cannula 211, thereby achieving the separation between the guide wire 22 and the auxiliary implantation part 11 of the flexible neural electrode 1. As shown in part (b) of FIG. 6, the auxiliary implantation assembly 2 is removed from the target implant, and the flexible neural electrode 1 is retained inside the target implant. Finally, the cannula assembly 21 is removed from the skull slit to complete the implantation of the flexible neural electrode 1. This method can perform implantation through a small incision on the target object, and ensure that the electrode is flatly adhered to the surface of the target implant by means of the guide wire 22 and the cannula assembly 21.

Through the above-mentioned implantation method, the objective of implanting the flexible neural electrode 1 through a relatively small slit opened on the target object can be achieved. The flexible neural electrode 1 may be precisely implanted into the intended target area after transitioning from the curled state to the unfolded state. It can be flatly adhered to the intended target area. This reduces the impact of the auxiliary implantation assembly 2 on the surface of the target implant, and enables the low-damage and precise implantation of the flexible neural electrode 1, thereby addressing the existing challenges associated with the implantation of the flexible neural electrode 1, namely significant damage and difficulty in achieving flat adherence.

In some embodiments, the step S102 of extending the distal end of the guide wire 22 from the distal end of the inner cannula 211 specifically includes: directly acting on the guide wire 22 to extend the distal end of the guide wire 22 from the distal end of the inner cannula 211. As shown in FIG. 5 and FIG. 6, FIG. 5 and FIG. 6 show schematic diagrams of operations of the implantation method for the implantation system according to the first embodiment, which directly acts on the guide wire 22 and does not act on the outer cannula 212, achieving the extension of the distal end of the guide wire 22 from the distal end of the inner cannula 211 to implant the flexible neural electrode 1.

The embodiment of the present application also provides another implantation method for an implantation system, which is applied to the above-mentioned implantation system for implanting the flexible neural electrodes.

Figure 9:
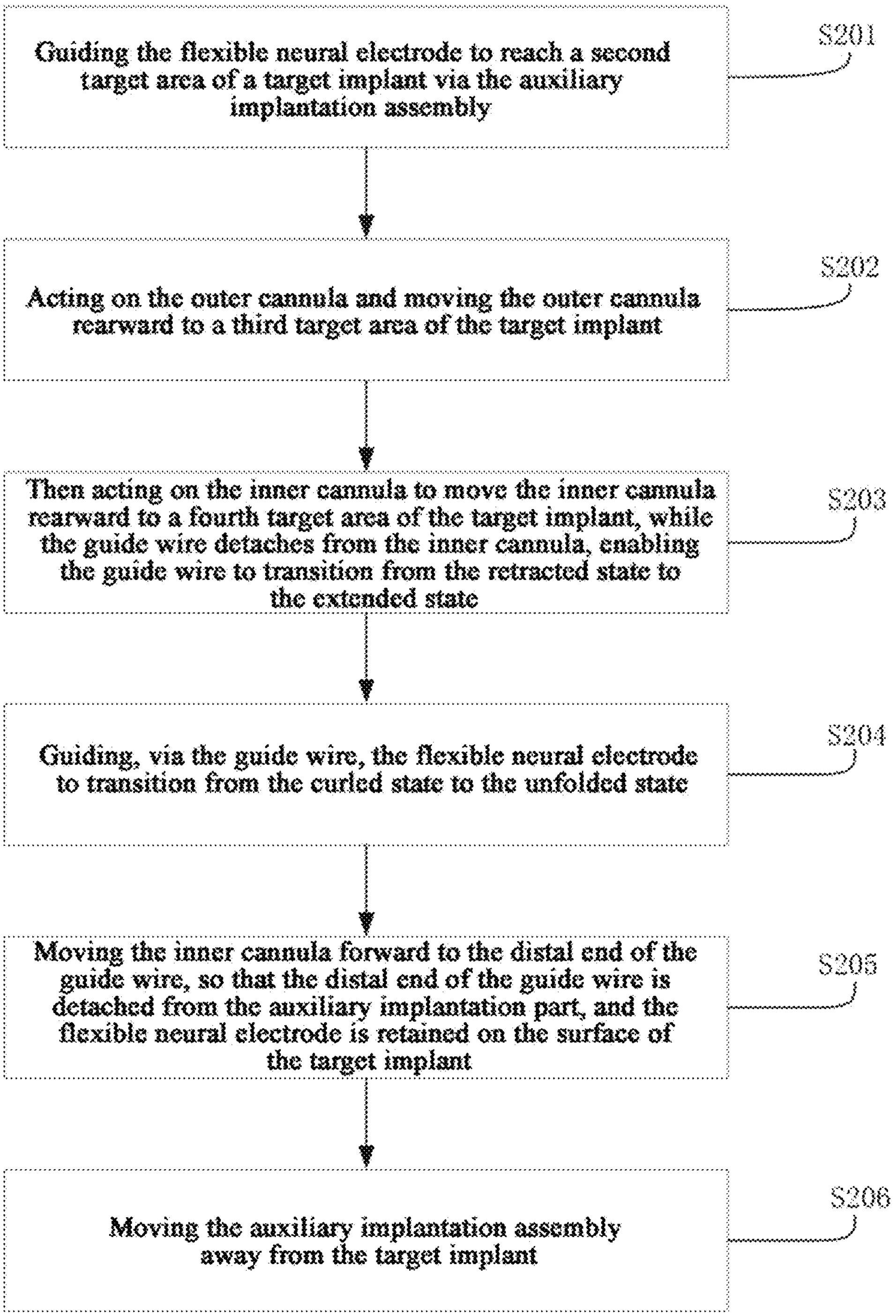
FIG. 9 is a second flowchart of an implantation method for an implantation system according to an embodiment of the present application.

As shown in FIG. 9, the implantation method includes steps S201 to S206.

Step S201: guiding the flexible neural electrode 1 to reach a second target area of the target implant via the auxiliary implantation assembly 2; wherein, the second target area is the intended target area.

Step S202: acting on the outer cannula 212 and moving the outer cannula 212 rearward to a third target area of the target implant.

Step S203: then acting on the inner cannula 211 to move the inner cannula 211 rearward to a fourth target area of the target implant, while the guide wire 22 detaches from the inner cannula 211, enabling the guide wire 22 to transition from the retracted state to the extended state.

Step S204: guiding, via the guide wire 22, the flexible neural electrode 1 to transition from the curled state to the unfolded state.

Step S205: moving the inner cannula 211 forward to the distal end of the guide wire 22, so that the distal end of the guide wire 22 is detached from the auxiliary implantation part 11, and the flexible neural electrode 1 is retained on the surface of the target implant.

Step S206: moving the auxiliary implantation assembly 2 away from the target implant.

In some embodiments, the fourth target area is closer to the second target area relative to the third target area.

As shown in FIG. 7, FIG. 7 shows schematic diagram of operations of the implantation method for the implantation system of the second embodiment, in which the implanted flexible neural electrode 1 is exemplified as a flexible spinal cord electrode. As shown in part (a) of FIG. 7, the inner cannula 211 and the guide wire 22 retracted into the inner cannula 211 are placed on the front or back of the electrode site part 14 of the flexible neural electrode 1, and aligned with the auxiliary implantation part 11 of the flexible neural electrode 1. After alignment, the guide wire 22 is moved axially from the proximal end of the inner cannula 211 to the distal end of the inner cannula 211 until the guide wire 22 penetrating out of the distal end of the inner cannula 211 is anchored to the auxiliary implantation part 11 of the flexible neural electrode 1, and the proximal guide wire 22 and the proximal end of the inner cannula 211 are fixed by means of the first connection structure 3. The flexible neural electrode 1 is curled around the inner cannula 211, and the curled flexible neural electrode 1 is spatially constrained by the outer cannula 212, forming a composite structure of the flexible neural electrode 1 and the auxiliary implantation assembly 2.

As shown in part (b) of FIG. 7, the auxiliary implantation assembly 2 draws the flexible neural electrode 1 to implant it into the second target area of the target implant, and the outer cannula 212 moves backwards and retracts to the third target area of the target implant.

As shown in part (c) of FIG. 7, the inner cannula 211 moves backwards and retracts to the fourth target area of the target implant. The guide wire 22 is transitioned from the retracted state to the extended state and corresponds to the shape of the flexible neural electrode 1. Meanwhile, the flexible neural electrode 1 is guided to transition from the curled state to the unfolded state.

As shown in part (d) of FIG. 7, after the flexible neural electrode 1 is fully extended, the inner cannula 211 is moved forward until it reaches the distal end of the guide wire 22, so that the distal end of the guide wire 22 is retracted into the inner cannula 211, thereby achieving the separation between the guide wire 22 and the auxiliary implantation part 11 of the flexible neural electrode 1.

As shown in part (e) of FIG. 7, the auxiliary implantation assembly 2 is removed from the target implant, and the flexible neural electrode 1 is retained on the surface of the target implant. Finally, the auxiliary implantation assembly 2 is removed from the skull slit to complete the implantation of the flexible neural electrode 1. This method can perform implantation through a small incision on the target object, and ensure that the electrode is flatly adhered to the surface of the target implant by means of the supporting members of the guide wire 22, the inner cannula 211 and the outer cannula 212.

Furthermore, although exemplary embodiments have been described herein, their scope comprises any and all embodiments with equivalent elements, modifications, omissions, combinations (e.g., solutions where various embodiments intersect), adaptations or changes based on the present application. The elements in the claims are to be broadly interpreted based on the language adopted in the claims, and are not limited to the examples described in this specification or during the implementation of the present application, and their examples are to be interpreted as non-exclusive.

The above description is intended to be illustrative rather than limiting. For example, the above examples (or one or more solutions thereof) may be used in combination with each other. For example, other embodiments may be used by those skilled in the art upon reading the above description. In addition, in the above specific embodiments, various features may be grouped together to simplify the present application. This should not be interpreted as an intention that an unclaimed disclosed feature is essential to any claim. On the contrary, the subject matter of the invention may be less than all features of a particular disclosed embodiment. Thus, the claims are incorporated into the detailed description here as examples or embodiments, wherein each claim stands alone as a separate embodiment, and it is considered that these embodiments may be combined with each other in various combinations or permutations. The scope of the invention should be determined with reference to the appended claims along with the full scope of equivalents to which these claims are entitled.

The above embodiments are only exemplary embodiments of the present application, and are not used to limit the invention, and the protection scope of the invention is defined by the claims. Those skilled in the art can make various modifications or equivalent substitutions within the spirit and protection scope of the invention, and such modifications or equivalent substitutions should also be regarded as falling within the protection scope of the invention.

The invention claimed is:

1. An implantation system for implanting a flexible neural electrode, wherein the implantation system comprises:

a flexible neural electrode on which an auxiliary implantation part is provided; and an auxiliary implantation assembly comprising a cannula assembly and a guide wire, the cannula assembly comprises an inner cannula and an outer cannula sleeved outside the inner cannula, the guide wire is made of a shape memory material and has a retracted state in which it is retracted within the inner cannula and an extended state in which it penetrates out of a distal end of the inner cannula, and an extended end of the guide wire is connected to the auxiliary implantation part, wherein, when the guide wire is in the retracted state, the flexible neural electrode is in a curled state in which it is curled between the inner cannula and the outer cannula, when the guide wire is in the extended state, the guide wire is configured to form a target shape conforming to an outer contour of the flexible neural electrode under the influence of the environment, and the flexible neural electrode moves to an intended target area along with the guide wire and unfolds, so as to transition from the curled state to an unfolded state, thereby enabling the flexible neural electrode to be flatly adhered to the intended target area;

wherein a bent part is formed at a distal end of the guide wire, and the bent part is penetrated through the auxiliary implantation part, so as to drive the flexible neural electrode to move via the guide wire.

2. The implantation system for implanting the flexible neural electrode according to claim 1, wherein the auxiliary implantation part of the flexible neural electrode is a hole or a slit.

3. The implantation system for implanting the flexible neural electrode according to claim 1, wherein, when a length of a part of a distal end of the guide wire penetrating out of the distal end of the inner cannula is not greater than a first threshold value, the guide wire is in the retracted state, when the length of the part of the distal end of the guide wire penetrating out of the distal end of the inner cannula is greater than the first threshold value, the guide wire transitions from the retracted state to the extended state.

4. The implantation system for implanting the flexible neural electrode according to claim 1, wherein the flexible neural electrode includes a signal transmission part and an electrode site part, and the electrode site part is electrically interconnected with a recording circuit and/or a stimulation circuit through the signal transmission part, so as to record neural signals via the recording circuit, and/or modulate neural signals via the stimulation circuit.

5. The implantation system for implanting the flexible neural electrode according to claim 4, wherein the signal transmission part includes a plurality of flexible insulating layers and a metal signal wire layer provided between adjacent flexible insulating layers, the metal signal wire layer is at least one layer, and the flexible insulating layer wraps the metal signal wire layer.

6. The implantation system for implanting the flexible neural electrode according to claim 5, wherein the flexible insulating layer is made of a flexible polymer material, the flexible polymer material comprises at least one of polyimide materials, polymeric polymer materials, photosensitive polymers, fluorine-containing polymers, and combinations thereof.

7. The implantation system for implanting the flexible neural electrode according to claim 1, wherein the auxiliary implantation part is provided at a distal end of the flexible neural electrode, and/or, the auxiliary implantation part is provided at a position in the middle of or adjacent to one side of the distal end of the flexible neural electrode.

8. The implantation system for implanting the flexible neural electrode according to claim 1, wherein a proximal end of the inner cannula is provided with a first connection structure connected to a proximal end of the guide wire, so as to define a relative position of the guide wire and the inner cannula during implantation process, and/or, a proximal end of the outer cannula is provided with a second connection structure connected to the proximal end of the inner cannula, so as to define a relative position of the outer cannula and the inner cannula during the implantation process.

* * * * *